United States Patent
Che et al.

(10) Patent No.: US 7,482,478 B2
(45) Date of Patent: Jan. 27, 2009

(54) DIASTEREOSELECTIVE EPOXIDATION OF ALLYLICALLY SUBSTITUTED ALKENES USING METALLOPORPHYRIN CATALYSTS

(75) Inventors: Chi-Ming Che, Hong Kong (CN); Man-Kin Wong, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 601 days.

(21) Appl. No.: 11/080,436

(22) Filed: Mar. 16, 2005

(65) Prior Publication Data

US 2005/0209470 A1 Sep. 22, 2005

Related U.S. Application Data

(60) Provisional application No. 60/553,972, filed on Mar. 18, 2004.

(51) Int. Cl.
C07D 301/12 (2006.01)
(52) U.S. Cl. ..................................... 549/531; 549/524
(58) Field of Classification Search ................ 549/524, 549/531, 532
See application file for complete search history.

(56) References Cited

OTHER PUBLICATIONS

Stephane Demay, et al., "Enantioselective Preparation of a Novel Chiral 1,2-Diamine," Synthesis (2001) No. 6, pp. 863-866.
Tracey L. Hutchison, et al., "Stereoselective Synthesis of a Conformationally Defined Cyclohexyl Carnitine Analogue that Binds CPT-1 with High Affinity," Bioorganic & Medicinal Chemistry 7, 1999, pp. 1505-1511.
Dae-Ro Ahn, et al., "Synthesis of Cyclopentane Amid DNA (cpa-DNA) and Its Pairing Properties," J. Org. Chem. 2003, pp. 7693-7699.
Hiroshi Tanaka, et al., "A New Approach to Nine-Membered Enediyne Using a Palladium Catalyzed Cross-Coupling Reaction," Synlett, Apr. 1997, pp. 381-383.
Toru Tachihara, et al., "Total synthesis of (+)-epiepoformin, (+)-epiepoxydon and (+)-bromoxone employing a useful chiral building block, ethyl (1R,2S)-5,5-ethylenedioxy-2-hydroxycyclohexanercarboxylate," Tetrahedron 59 (2003) pp. 1773-1780.
Arun K. Ghosh, et al., "Synthesis of FDA Approved HIV Protease Inhibitor," Synthesis (2001) No. 15, pp. 2203-2229.
Oliver Block, et al., "New Stereoselective Route to the Epoxyquinol Core of Manumycin-Type Natural Products. Synthesis of Enantiopure (+)-Bromoxone, (−)-LL-C10037α, and (+)-KT ," J. Org. Chem., pp. 716-721 (2000).
Chaomin Li, et al., "Total Synthesis of the NF-κ B Inhibitor (−)-Cycloepoxydon: Utilization of Tartrate-Mediated Nucleophilic Expoxidation," J. Am. Chem. Soc. (2001) pp. 11308-11309.
Mitsuru Shoji, et al., "Total Synthesis of (+)-Epoxyquinols A and B," Angew. Chem. Int. Ed. (2002) pp. 3192-3194.
David A. Evans, et al., "Substrate-Directable Chemical Reactions," Chem. Rev. (1993) pp. 1307-1370.

Waldemar Adam, et al., "Hydroxy Group Directivity in the Epoxidation of Chiral Allylic Alcohols: Controls of Diastereoselectivity through Allylic Strain and Hydrogen Bonding," Acc. Chem. Res. (1999) pp. 703-710.
Peter O'Brien, et al., "cis-and trans-Stereoselective Expoxidation of N-Protected 2-Cyclohexen-1-ylamines," Organic Letters (2003) vol. 5, No. 26, pp. 4955-4957.

(Continued)

*Primary Examiner*—Bernard Dentz
(74) *Attorney, Agent, or Firm*—Robert D. Katz; Cooper & Dunham LLP

(57) ABSTRACT

Diastereoselective epoxidation of allylically substituted alkenes using metalloporphyrins as catalyst provides high trans-selectivities (i.e., trans-:cis-epoxide ratio). A diversity of cycloalkenes bearing different allylic substituents are shown to be efficiently epoxidized to afford the corresponding trans-epoxides with excellent trans-selectivities (up to >98%) and good yields (up to 99%). Acyclic allylic alkenes bearing different allylic substituents are efficiently epoxidized to afford the corresponding erythro-epoxides with good erythro-selectivities. The metalloporphyrin-catalyzed reactions exhibit up to 20 times higher trans-selectivities than the conventional method using m-chloroperoxybenzoic acid as oxidant.

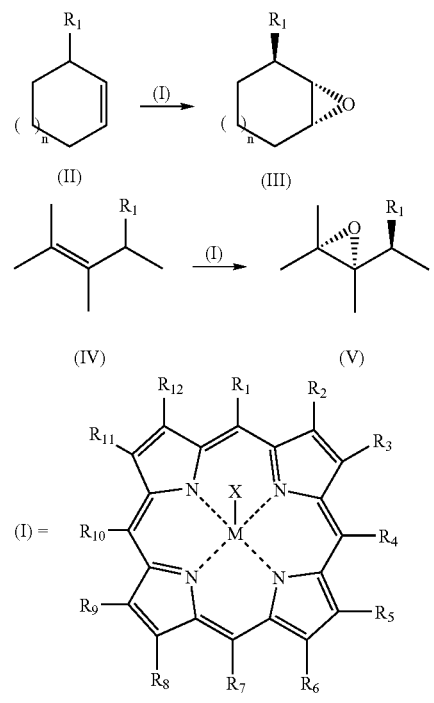

9 Claims, 1 Drawing Sheet

OTHER PUBLICATIONS

Masaaki Kurihara, et al., "Stereoselective Expoxidation with Dioxiranes Generated from Ketones," Tetrahedron Letters. vol. 35, No. 10, (1994) pp. 1577-1580.

Robert W. Murray, et al., "Solvent Tuning of Diastereoselectivity in Dimethyldioxirane Epoxidation Reaction," Tetrahedron Letters, vol. 36, No. 14 (1995) pp. 2437-2440.

Robert W. Murray, et al., "Diastereoselectivity in the Expoxidation of Substituted Cyclohexenes by Dimethyldioxirane," J. Org. Chem (1996) pp. 1830-1841.

Dan Yang, et al., "Diastereoselective Epoxidation of Cyclohexene Derivatives by Dioxiranes Generated in Situ. Importance of Steric and Field Effects," J. Org. Chem. (1999), pp. 1635-1639.

Waldemar Adam, et al., "Steric and Electronic Effects in the Disastereoselective Catalytic Epoxidation of Cyclic Allylic Alcohols with Methyltrioxorhenium (MTO)," Eur. J. Org. Chem (1999) pp. 785-790.

Bernard Meunier, "Metalloporphyrins as Versatile Catalysts for Oxidation Reactions and Oxidative DNA Cleavage," Chem. Rev. (1992) pp. 1411-1456.

D. Mansuy, "Activation of alkanes: the biomimetic approach," Coordination Chemistry Reviews (1993) pp. 129-142.

David Dolphins, et al., "Polyhaloporphyrins: Unusual Ligands for Metals and Metal-Catalyzed Oxidations," Acc. Chem. Res. (1997) pp. 251-259.

John T. Groves, et al., "Epoxidation Reactions Catalyzed by Iron Porphyrins. Oxygen Transfer from Iodosylbenzene," J. Am. Chem. Soc. (1983) pp. 5786-5791.

James P. Collman, et al., "Epoxidation of Olefins by Cytochrome P-450 Model Compounds: Kinetics and Stereochemistry of Oxygen Atom Transfer and Origin of Shape Selectivity," J. Am. Chem. Soc. (1985) pp. 2000-2005.

John T. Groves, et al., "Membrane-Spanning Steroidal Metalloporphyrins as Site-Selective Catalysts in Synthetic Vesicles," J. Am. Chem. Soc. (1987) pp. 5045-5047.

James P. Collman, et al., Shape-Selective Olefin Epoxidation Catalyzed by Manganese Picnic Basket Porphyrins, J. Am. Chem. Soc. (1990) pp. 5356-5357.

John T. Groves, et al., "Catalytic Asymmetric Epoxidations with Chiral Iron Porphyrins," J. Am. Chem. (1983) pp. 5791-5796.

D. Mansuy, et al., "Asymmetric Epoxidation of Alkenes catalysed by a 'Basket-handle' Iron-Porphyrin bearing Amino Acids," J. Chem. Soc. Chem. Comm. (1985) pp. 155-156.

Sean O'Malley, et al., "Synthesis and Characterization of the "Chiral Wall" Porphyrin: A Chemically Robust Llgand for Metal-Catalyzed Asymmetric Epoxidation," J. Am. Chem. Soc. (1989) pp. 9116-9117.

John T. Groves, et al., "Asymmetric Hydroxylation, Epoxidation, and Sulfoxidation Catalyzed by Vaulted Binaphthyl Metalloporphyrins," J. Org. Chem. (1990) pp. 3628-3634.

Yoshinori Naruta, et al., "Catalytic and Asymmetric Epoxidation of Olefins with Iron Complexes of "Twin-Coronet" Porphyrins. A Mechanistic Insight into the Chiral Induction of Styrene Derivatives," J. Am. Chem. Soc. (1991) pp. 6865-6872.

Ronald L. Halterman, et al., "Catalytic Asymmetric Epoxidation of Unfunctionalized Alkenes Using the First $D_4$_Symmetric Metallotetraphenylporphyrin," J. Org. Chem. (1991) pp. 5253-5254.

Katsuaki Konishi, et al., "Asymmetric Epoxidation of Olefins Catalyzed by Manganese Complexes of Chiral "Strapped" Porphyrins with Diastereotopic Faces. A Novel Strategy for Stereochemical Modeling of the Active Site of Cytochrome P-450," J. Am. Chem. Soc. (1992) pp. 1313-1317.

James P. Collman, et al., "Regioselective and Enantioselective Epoxidation Catalyzed by Metalloporphyrins," Science, New Series, (1993) pp. 1404-1411.

James P. Collman, et al., "An Efficient Catalyst for Asymmetric Epoxidation of Terminal Olefins," J. Am. Chem. Soc. (1999) pp. 460-461.

Zeev Gross, et al, "Remarkable Effects of Metal, Solvent, and Oxidant on Metalloporphyrin-Catalyzed Enantioselective Epoxidation of Olefins," J. Org. Chem. (1997) pp. 5514-5521.

Albrecht Berkessel, et al., "Catalytic asymmetric epoxidation with a chiral ruthenium porphyrin and N-Oxides," J. Chem. Soc. , Perkin Trans. (1997) pp. 2265-2266.

Zeev Gross, et al., "Asymmetric Catalysis by a Chiral Ruthenium Porphyrin: Epoxidation, Hydroxylation, and Partial Kinetic Resolution of Hydrocarbons," Organic Letters, vol. 1, No. 13 (1999) pp. 2077-2080.

Rui Zhang, et al., "Enantioselective epoxidation of trans-disubstitued alkenes by $D_2$_-symmetric chiral dioxoruthenium(vi) porphyrins," Chem. Communication (1999) pp. 409-410.

Zeev Gross, et al., "Dual Role of Pyridine N-Oxides in Ruthenium Porphyrin-Catalyzed Asymmetric Epoxidation of Olefins," Inorg. Chem. (1999) pp. 1446-1449.

Rui Zhang, et al., "Highly Efficient Asymmetric Epoxidation of Alkenes with a $D_4$-Symmetric Chiral Dichlororuthenium(IV) Porphyrin Catalyst," J. Org. Chem. (2001) pp. 8145-8153.

Rui Zhang, et al., "Stereo- and Enantioselective Alkene Epoxidations: A Comparative Study of $D_4$_ and $D_2$_Symmetric Homochiral trans-Dioxoruthenium(vi) Porphyrins," Chem. Eur. J. (2002) pp. 2495-2507.

John T. Groves, et al., "Rapid Catalytic Oxygenation of Hydrocarbons by Ruthenium Pentafluorophenylporphyrin Complexes: Evidence for the Involvement of a Ru(III) Intermediate," J. Am. Chem. Soc. (1996) pp. 8961-8962.

Chun-Jing Liu, et al., "Ruthenium porphyrin encapsulated in modified mesoporous molecular sieve MCM-41 for alkene oxidation," Chem. Comm. (1997) pp. 65-66.

Chun-Jing Liu, et al., "Ruthenium meso-Tetrakis(2,6-dichlopheny) porphyrin Complex Immobilized in Mesoporous MCM-41 as a Heterogeneous Catalyst for Selective Alkene Epoxidations," J. Org. Chem. (1998) pp. 7364-7369.

Xiao-Qi Yu, et al., "Polymer-Supported Ruthenium Porphyrins: Versatile and Robust Epoxidation Catalysts with Unusual Selectivity," J. Am. Chem. Soc. (2000) pp. 5337-5342.

Jun-Long Zhang, et al., "Soluble Polymer-Supported Ruthenium Porphyrin Catalysts for Epoxidation Cyclopropanation, and Aziridination of Alkenes," Organic Letters, vol. 4, No. 11, (2002) pp. 1911-1914.

Waldermar Adam, et al., "Regio-and Diastereoselective Epoxidation of Chiral Allylic Alcohols Catalyzed by Manganese(salen) and Iron(porphyrin) Complexes," J. Am. Chem. Soc. (1999), pp. 1879-1882.

P. Battioni, et al., "Monooxygenase-like Oxidation of Hydrocarbons by $H_2O_2$ Catalyzed by Manganese Porphyrins and Imidazole: Selection of the Best Catalytic System and Nature of the Active Oxygen Species," J. Am. Chem. Soc. (1988) pp. 8462-8470.

Annie Thellend, et al., "Ammonium Acetate as a very Simple and Efficient Cocatalyst for Manganese Porphyrin-catalysed Oxygenation of Hydrocarbons by Hydrogen Peroxide," J. Chem. Soc., Chem. Comm. (1994) pp. 1035-1036.

Cyril Poriel, et al., "Syntheses of manganese and iron tetraspirobifluorene porphyrins a snew catalysts for oxidation of alkenes by hydrogen peroxide and iodosylbenzene," Tetrahedron Letters 44 (2003) pp. 1759-1761.

Benjamin S. Lane, et al., "A Cheap, Catalytic, Scalable, and Environmentally Benign Method for Alkene Epoxidations," J. Am. Chem. Soc., (2001) pp. 2933-2934.

Benjamin S. Lane, et al., "Manganese-Catalyzed Epoxidations of Alkenes in Bicarbonate Solutions," J. Am. Chem. Soc. (2002) pp. 11946-11954.

Masaaki Kurihara, et al., "Stereoselective Epoxidation of Acyclic Allylic Ethers Using Ketone-Oxone System," Chemistry Letters 1997, pp. 1015-1016.

David P. Rotella, "Stereoselective Synthesis of Erythro α-Amino Epoxides," Tetrahedron Letters, vol. 36, No. 31, (1995), pp. 5453-5456.

Lino Columbo, et al., "Stereoselective synthesis of 6,5-bicyclic reverse-turn peptidomimetics," Tetrahedron 54 (1998) pp. 5325-5336.

B. Moon Kim, et al., "Synthesis of a Chiral Aziridine Derivative as a Versatile Intermediate for HIV Protease Inhibitors," Organic Letters, vol. 3, No. 15, (2001) pp. 2349-2351.

Dengjin Wang, et al., "One-Carbon Chain Extension of Esters to α-Chloroketones: A Safer Route without Diazomethane," J. Org. Chem. (2004) pp. 1629-1633.

Kevin E.B. Parkes, et al., "Studies toward the Large-Scale Synthesis of the HIV Proteinase Inhibitor Ro 31-8959," J. Org. Chem. (1994) pp. 3656-3664.

Jonas Branalt, et al., "A Convenient Synthesis of 1-(S)-[1'-(S)-(t-Butyloxycarbonylamno)-2'-phenyltehyl]oxirane. A Useful Building Block in the Synthesis of HIV Protease Inhibitors," Tetrahedron Letters, vol. 38, No. 19, (1997) pp. 3483-3486.

Nuria Aguilar, et al., "A General, Catalytic, and Enantioselective Synthesis of (S)-γ-[(S)-1-Aminoalkyl]-γ-lactones," J. Org. Chem. (1998) pp. 3560-3567.

Masaaki Kurihara, et al., "Stereoselective Synthesis of an Erythro N-protected α-Amino Epoxide Derivative," Tetrahedron Letters 40 (1999) pp. 3183-3184.

Jay R. Luly, et al., "A Synthesis of Protected Aminoalkyl Epoxides from α-Amino Acids," J. Org. Chem. (1987) pp. 1487-1492.

Annika Jenmalm, et al., "Stereoselective Epoxidation of Phe-Gly and Phe-Phe Vinyl Isotheres," J. Org. Chem. (1994) pp. 1139-1148.

Sergio Romeo, et al., "Stereoselective Synthesis of Protected Amino alkyl Epoxides," Tetrahedron Letters, vol. 35, No. 28 (1994) pp. 4939-4942.

Anthony J. Pearson, et al., "Ester-Directed Alkene Functionalization. A Potential Approach to Trichothecene Synthesis," J. Org. Chem. (1986) pp. 2505-2511.

Communication to the Editor, "Protection of Hydroxyl Groups as tert-Butyldimethylsilyl Derivatives," Journal of American Chemical Society, (1972) pp. 6190-6191.

Michael R. Detty, et al., "Silyl Halides from (Phenylseleno)silanes. Reaction with Oxiranes and Alcohols to Give Hydrolytically Stable Silyl Ethers," J. Org. Chem. (1981) pp. 1283-1292.

Timothy T. Curran, et al., "The Preparation of Optically Active 2-Cyclopenten-1,4-Diol Derivatives from Furfuryl Alcohol," Tetrahedron vol. 53, No. 6, (1997) pp. 1983-2004.

Rolf A.T.M. Van Benthem, et al., "A Practical Synthesis of Geometrically Pure N-Boc-Protected Primary Allyllic Amines," Synlett, (1994) pp. 368-370.

Stephen G. Davies, et al., "A Convenient Synthesis of β-γ-Unsaturated Carboxylic Acids and Esters. The Isomeric 5-t-Butylcyclohex-2-enecarboxylic Acids," pp. 2279-2280, JCS Perkin I (1976).

Paolo Crotti, et al., "Synthesis and Ring-Opening Reactions of the Diastereoisomeric cis-and-trans Epoxides Derived from 3-(Benzyloxy)cyclopentene and 2-(Benzyloxy)-2,5-dihydrofuran," Euro. J. Org. Chem (1998) pp. 1675-1686.

Fritz Theil, "Chemoenzymatic Synthesis of Enantiomerically Pure β,γ-Disubstituted γ-Lactones," Tetrahedron: Asymmetry vol. 6, No. 7 (1995) p. 1693-1698.

1: M = Mn³⁺; X = Cl; Ar = (2,6-dichlorophenyl)   Mn(TDCPP)Cl

2: M = Ru²⁺; X = CO; Ar = (2,6-dichlorophenyl)   Ru(TDCPP)(CO)

3: M = Mn³⁺; X = Cl; Ar = (2,6-dimethylphenyl)   Mn(TMP)Cl

4: M = Mn³⁺; X = Cl; Ar = (pentafluorophenyl)   Mn(TPFPP)Cl

5: M = Mn³⁺; X = Cl; Ar = (4-methylphenyl)   Mn(TTP)Cl

DIASTEREOSELECTIVE EPOXIDATION OF ALLYLICALLY SUBSTITUTED ALKENES USING METALLOPORPHYRIN CATALYSTS

This is based on the priority of U.S. Provisional Application Ser. No. 60/553,972, filed Mar. 18, 2004.

FIELD OF THE INVENTION

This invention concerns the use of sterically bulky metalloporphyrins as efficient catalysts for diastereoselective epoxidation of allylically substituted alkenes.

BACKGROUND OF THE INVENTION

Development of efficient methods for highly diastereoselective epoxidation of allylically substituted alkenes is of great importance, as their epoxides are versatile building blocks for organic synthesis as well as construction of biologically active natural products and chiral drugs.

trans-Epoxides of some allylic alkenes are known to be key synthetic intermediates/starting materials in the preparation of synthetically useful chiral 1,2-diamines [Demay, S.; Kotschy, A.; Knochel, P. *Synthesis* 2001, 863], conformationally rigid analogues of Carnitine [Hutchison, T. L.; Saeed, A.; Wolkowicz, P. E.; McMillin, J. B.; Brouillette, W. J. *Bioorg. Med. Chem.* 1999, 7, 1505], cyclopentane analogues of DNA [Ahn, D.-R.; Mosimann, M.; Leumann, C. J. *J. Org. Chem.* 2003, 68, 7693], core structure of Neocarzinostain antibiotics [Tanaka, H.; Yamada, H.; Matsuda, A.; Takahashi, T. *Synlett.* 1997, 381], biologically active natural products such as (+)-epiepoformin [Tachihara, T.; Kitahara, T. *Tetrahedron* 2003, 59, 1773], and several best-selling FDA approved HIV-protease inhibitors [Ghosh, A. K.; Bilcer, G.; Schiltz, G. *Synthesis* 2001, 15, 2203].

In addition, some trans-epoxides of cycloalkenes are fundamental structural units of biologically active natural products such as (+)-bromoxone [Block, O.; Klein, G.; Altenbach, H.-J.; Brauer, D. J. *J. Org. Chem.* 2000, 65, 716], (−)-cycloepoxydon [Li, C.; Pace, E. A.; Liang, M.-C.; Lobkovsky, E.; Gilmore, T. D.; Porco, J. A., Jr. *J. Am. Chem. Soc.* 2001, 123, 11308], and (+)-epoxyquinols A and B [Shoji, M.; Yamaguchi, J.; Kakeya, H.; Osada, H.; Hayashi, Y. *Angew. Chem. Int. Ed.* 2002, 41, 3192].

Significant advances have been achieved in cis-selective epoxidation of allylic alcohols through hydrogen bonding between their syn-directing hydroxyl group and oxidants. In general, highly cis-selective epoxides (cis:trans-epoxide ratio>20:1) could be conveniently obtained by using peracids such as m-chloroperoxybenzoic acid (m-CPBA) as oxidant [for reviews on highly cis-selective epoxidation, see: Hoveyda, A. H.; Evans, D. A.; Fu, G. C. *Chem. Rev.* 1993, 93, 1307. Adam, W.; Wirth, T. *Acc. Chem. Res.* 1999, 32, 703].

For epoxidation of allylically substituted alkenes without syn-directing groups, trans-epoxides would be obtained as major product through steric interaction between the substrates and the oxidants. However, the trans-selectivity (i.e., trans:cis-epoxide ratio) obtained by using the common oxidants such as m-CPBA and dioxiranes are generally low (i.e., trans:cis<20:1). Thus, the development of efficient methods for highly trans-selective epoxidation of allylic alkenes poses an important challenge in organic synthesis.

Recently, a systematic study on m-CPBA-mediated diastereoselective epoxidation of some selected N-protected 2-cyclohexen-1-ylamines has been reported [O'Brien, P.; Childs, A. C.; Ensor, G. J.; Hill, C. L.; Kirby, J. P.; Dearden, M. J.; Oxenford, S. J.; Rosser, C. M. *Org. Lett.* 2003, 5, 4955].

Dioxiranes (either isolated or generated in situ from ketones and oxone) have been reported as mild and efficient oxidants for trans-selective epoxidation of allylically substituted alkenes [see: Miyata, N.; Kurihara, M.; Ito, S.; Tsutsumi, N. *Tetrahedron Lett.* 1994, 35, 1577. Murray, R. W.; Singh, M.; Williams, B. L.; Moncrieff, H. M. *Tetrahedron Lett.* 1995, 36, 2437. Murray, R. W.; Singh, M.; Williams, B. L.; Moncrieff, H. M. *J. Org. Chem.* 1996, 61, 1830. Yang, D.; Jiao, G.-S.; Yip, Y.-C.; Wong, M.-K. *J. Org. Chem.* 1999, 64, 1635]. Methyltrioxorhenium (MTO) has been employed for diastereoselective epoxidation of cyclic allylic alkenes [Adam, W.; Mitchell, C. M.; Saha-Moller, C. R. Eur. *J. Org. Chem.* 1999, 785]. The main reason for their low trans-selectivities could be attributed to the weak/moderate steric interaction between the oxidants and the substrates.

Metalloporphyrin-catalyzed alkene epoxidation has been a subject of extensive investigation [Meunier, B. *Chem. Rev.* 1992, 92, 1411. Mansuy, D. *Coord. Chem. Rev.* 1993, 125, 129. Dolphin, D.; Traylor, T. G.; Xie, L. Y. *Acc. Chem. Res.* 1997, 30, 251].

As will be appreciated from the foregoing, metalloporphyrin catalysts have been used for the enantioselective epoxidations of alkenes.

Metalloporphyrins have been used as catalysts for regio- and shape-selective epoxidations of alkenes [Groves, J. T.; Nemo, T. E. *J. Am. Chem. Soc.* 1983, 105, 5786. Collman, J. P.; Brauman, J. I.; Meunier, B.; Hayashi, T.; Kodadek, T.; Raybuck, S. A. *J. Am. Chem. Soc.* 1985, 107, 2000. Groves, J. T.; Neumann, R. *J. Am. Chem. Soc.* 1987, 109, 5045. Collman, J. P.; Zhang, X.; Hembre, R. T.; Brauman, J. I. *J. Am. Chem. Soc.* 1990, 112, 5356.]

Chiral iron and manganese porphyrins have been employed for enantioselective alkene epoxidations [Groves, J. T.; Myers, R. S. *J. Am. Chem. Soc.* 1983, 105, 5791. Mansuy, D.; Battoni, P.; Renaud, J. P.; Guerin, P. *J. Chem. Soc., Chem. Commun.* 1985, 155. O'Malley, S. Kodadek, T. *J. Am. Chem. Soc.* 1989, 111, 9176. Grove, J. T.; Viski, P. *J. Org. Chem.* 1990, 55, 3628. Naruta, Y.; Tani, F.; Ishihara, N.; Maruyama, K. *J. Am. Chem. Soc.* 1991, 113, 6865. Halterman, R. L.; Jan, S.-T. *J. Org. Chem.* 1991, 56, 5253. Knoishi, K.; Oda, K.-I.; Nishida, K.; Aida, T.; Inoue, S. *J. Am. Chem. Soc.* 1992, 114, 1313. Collman, J. P.; Zhang, X.-M.; Lee, V. J.; Uffelman, E. S.; Brauman, J. I. *Science* 1993, 261, 1404. Collman, J. P.; Wang, Z.; Straumanis, A.; Quelquejeu, M. *J. Am. Chem. Soc.* 1999, 121, 460.]

Chiral ruthenium-porphyrin have been used as efficient catalysts for enantioselective epoxidation of alkenes [Gross, Z.; Ini, S. *J. Org. Chem.* 1997, 62, 5514. Berkessel, A.; Frauenkron, M. *J. Chem. Soc., Perkin Trans.* 1, 1997, 2265. Gross, Z.; Ini, S. *Org. Lett.* 1999, 1, 2077. Zhang, R.; Yu, W.-Y.; Lai, T.-S.; Che, C.-M. *Chem. Commun.* 1999, 409. Gross, Z.; Ini, S. *Inorg. Chem.* 1999, 38, 1446. Zhang, R.; Yu, W.-Y.; Wong, K.-Y.; Che, C.-M. *J. Org. Chem.* 2001, 66, 8145. Zhang, R.; Yu, W.-Y.; Sun, H.-Z.; Liu, W.-S.; Che, C.-M. *Chem. Eur. J.* 2002, 8, 2495.]

In addition, it has been reported that supported polyhalogenated metalloporphyrins are robust and recyclable catalysts for alkene epoxidations with exceptionally high turnover numbers [Groves, J. T.; Bonchio, M.; Carofiglio, T.; Shalyaev, K. *J. Am. Chem. Soc.* 1996, 118, 8961. Liu, C.-J.; Li, S.-G.; Pang, W.-Q.; Che, C.-M. *Chem. Commun.* 1997, 65. Che, C.-M.; Liu, C.-J.; Yu, W.-Y.; Li, S.-G. *J. Org. Chem.* 1998, 63, 7364. Che, C.-M.; Yu, X.-Q.; Huang, J.-S.; Yu, W.-Y. *J. Am. Chem. Soc.* 2000, 122, 5337. Che, C.-M.; Zhang, J.-L. *Org. Lett.* 2002, 4, 1911].

However, there is a paucity of reports of the use of metalloporphyrin catalysts for diastereoselective epoxidation of allylically substituted alkenes. It has been reported that high diastereoselectivity could be obtained in epoxidation of 3,4,6-tri-O-acetyl-D-glucal and 2-(Boc-amino)-1-phenylbut-3-ene using ruthenium-porphyrins as catalysts [Che, C.-M.; Liu, C.-J.; Yu, W.-Y.; Li, S.-G. *J. Org. Chem.* 1998, 63, 7364. Che, C.-M.; Yu, X.-Q.; Huang, J.-S.; Yu, W.-Y. *J. Am. Chem. Soc.* 2000, 122, 5337. Che, C.-M.; Zhang, J.-L. *Org. Lett.* 2002, 4, 1911]. There is exclusive formation of α-epoxide in the epoxidation of 3,4,6-tri-O-acetyl-D-glucal, which we believe could be attributed to the strong steric interaction between the bulky porphyrin ligand and the three O-acetyl groups on the substrate's ring. On the other hand, the threo-selectivity obtained in the epoxidation of 2-(Boc-amino)-1-phenylbut-3-ene appears to be due to the hydrogen bonding formation between the NHBoc group of the substrate and the metal oxo center of the porphyrin catalysts.

Iron porphyrins have been reported as catalysts in diastereoselective epoxidation of some hydroxy-protected acyclic chiral allylic alcohols, see: Adam, W.; Stegmann, V. R.; Saha-Moller, C. R. *J. Am. Chem. Soc.* 1999, 121, 1879. For these hydroxy-protected allylic alcohols, erythro selectivity was obtained in the epoxidation. The erythro selectivity could be attributed to steric effects between the substrates and the catalysts.

In view of the significance of trans-selective epoxides of allylically substituted alkenes in the synthesis of natural products and chiral drugs, there exists an urgent need to develop new, practical, and efficient methods for the synthesis of these synthetically useful epoxides.

DETAILED DESCRIPTION OF THE INVENTION

Figure 1:
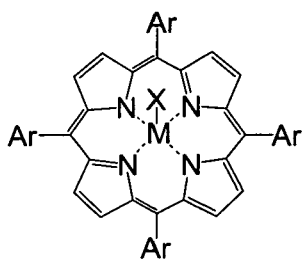
FIG. 1 sets forth five metalloporphyrins which can be used in the present invention.

In this invention, highly trans-selective epoxidation is achieved based on strong steric interaction between the substrate and the bulky porphyrin ligand when the substrate and ligand are appropriately selected.

In broad terms, the method for synthesizing a trans-/erythro-epoxide from an allylically substituted alkene involves catalyzing the reaction of an oxidant with the alkene in the presence of a catalytic amount of metalloporphyrin as the catalyst for producing the epoxide. To preferentially achieve a trans-/erythro-epoxide, the alkene and catalyst must be appropriately selected. Other than in the selection of the alkene and catalyst, the reagents and processes of the prior art can be employed.

The alkene used in this invention is an allylically substituted alkene of the formula R—CH($R_1$)—CH=CH—CH—R in which $R_1$ is a suitable allylic substituent. Each of the carbon atoms in the R groups of these alkenes is optionally substituted and two R groups can be linked to form with the carbon atoms to which they are attached, a 5-, 6-, 7-, 8- or 9-membered ring, which itself can be fused to another ring.

Thus, the alkene can be a cyclic allylically substituted alkene (for example: formula II) or an acyclic allylically substituted alkene (for example: formula IV):

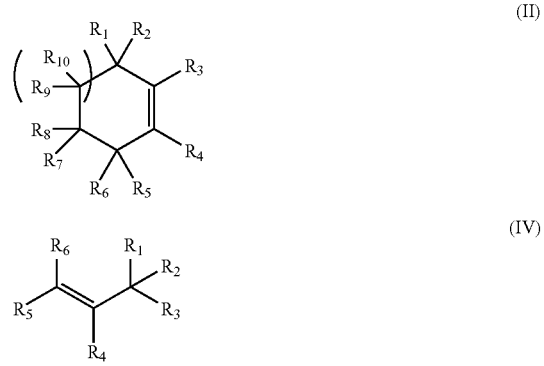

wherein $R_1$ is an allylic substituent selected from the group consisting of halogen, heteroatom, hydroxy, alkoxy, substituted hydroxy, carboxyl, carbonyl, cyano, silyl, boro, amino, substituted amino, nitro, alkyl, substituted alkyl, aryl, substituted aryl, heteroaryl, substituted heteroaryl and phosphorus groups; each of $R_2$-$R_{10}$ is individually selected from the group consisting of hydrogen, halogen, heteroatom, hydroxyl, alkoxy, substituted hydroxy, carboxyl, carbonyl, cyano, silyl, boro, amino, substituted amino, nitro, alkyl, substituted alkyl, aryl, substituted aryl, heteroaryl, and substituted heteroaryl groups; and $R_5$ and $R_6$ in formula II can also be an oxo group. In formula II, the ring can be five-membered, seven-membered, eight-membered, or nine-membered (i.e., n can be 0, 1, 2, 3 or 4), or the R substituents can be linked to form a fused ring. Without limiting the foregoing, the heteroatom can be, for instance, oxygen, nitrogen, silicon, boron, selenium, phosphorus or sulfur and the substituents on the various moieties which are substituted can be alkyl, aryl, halogen, hydroxy, oxo, alkoxy, carboxyl, carbonyl, cyano, amino, nitro, heteroalkyl and/or heteroaryl.

Beyond the examples of alkenes described later in this specification, some of the alkenes that can be employed include:

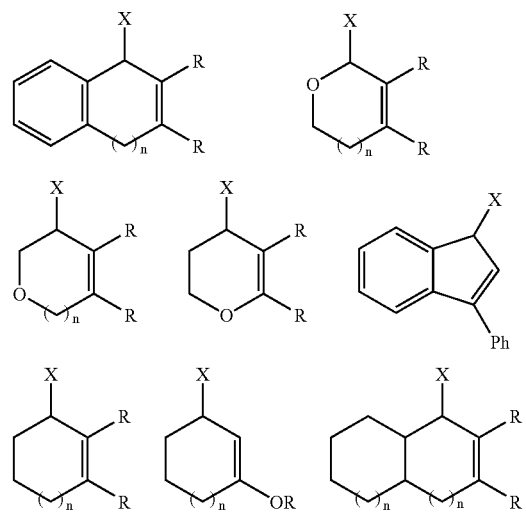

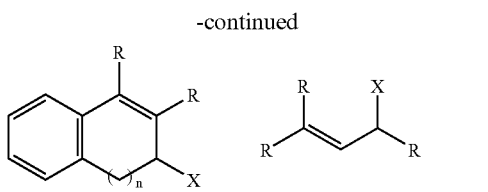

in which X is O, N, C, Br, Cl, I, CN, Si, B, Se, NO$_2$, SO$_2$Ph and P; R is H, alkyl, aryl, heteroalkyl, and hetero aryl; and n is 0 to 4;

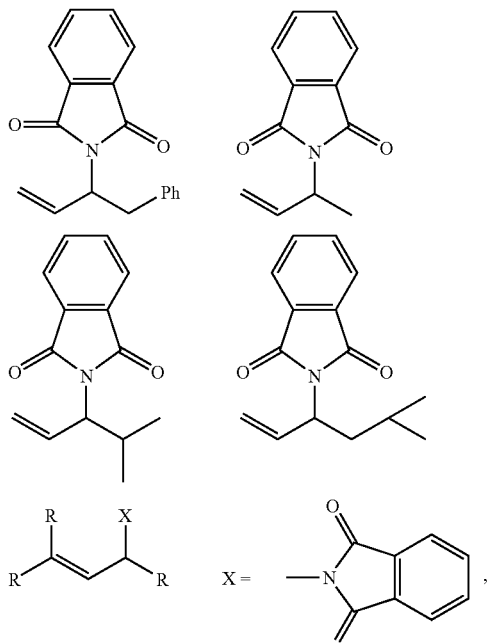

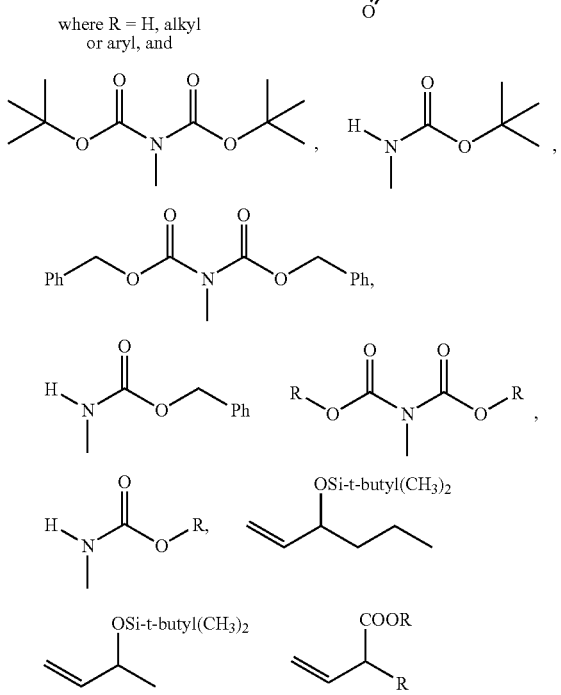

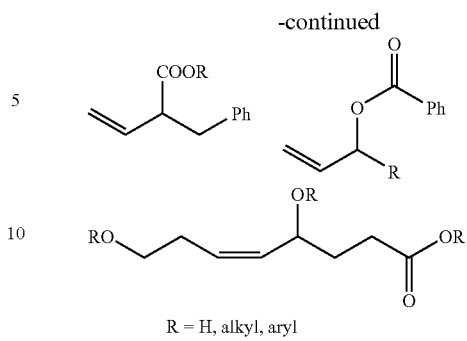

R = H, alkyl, aryl

The metalloporphyrin can be a metal complex of the formula (I):

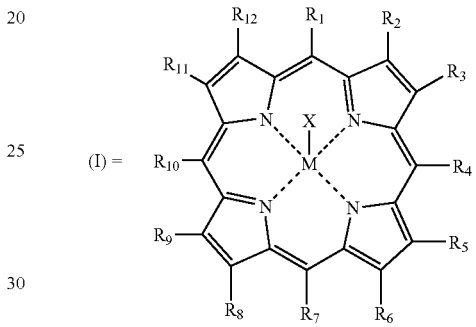

in which M is selected from Mn, Ru, Fe, Os, Rh, Ir, Nb, Mo, Ti or Re; X is selected from Cl, CO, O$^{2-}$(oxo), N$^{3-}$(nitrido), NR(imide) (where R=alkyl, aryl, sulfonyl or acetyl), or a weakly coordination ligand; and where R$_1$-R$_{12}$ is selected from various substituents that may be the same or different, and are each independently selected from the group consisting of hydrogen, halogen, heteroatom, alkyl, substituted alkyl, aryl, substituted aryl, heteroaryl and substituted heteroaryl groups. Without limiting the foregoing, the heteroatom can be, for instance, oxygen, nitrogen or sulfur and the substituents on the various moieties which are substituted can be alkyl, aryl, halogen, hydroxy, oxo, alkoxy, carboxyl, carbonyl, cyano, amino, amino, nitro, heteroalkyl and/or heteroaryl. Typical catalysts are set forth in FIG. 1.

Such catalysts can be linked to an inert solid support to function as recyclable catalysts (such as Merrifield resin, polyethylene glycol resin, dendrimer, and MCM-41).

Without being limited to theory, it appears that the relative size of the ortho substituent on the phenyl groups of the porphyrin rings and the R$_1$ and any substituent adjacent the unsaturation of the alkene have the greatest influence on selectivity. The trans selectivity has been noted to usually increase as the steric size of the alkene R$_1$ and ortho substituents increased. It is preferred to select these groups so as to permit the approach of the alkene to the metallic center of the catalyst, whether head-on or side-on, with minimal steric obstruction.

The method can be conducted in the presence of a solvent such as acetonitrile, water, dichloromethane, chloroform, methanol, t-butanol, benzene, toluene, xylene, chlorobenzene or their mixtures.

Typical oxidants include hydrogen peroxide and its derivatives, oxone (2KHSO$_5$·KHSO$_4$·K$_2$SO$_4$), 2,6-dichloropyridine N-oxide, peracids, sodium hypochlorite, t-butyl hydroperoxide, iodosylbenzene, oxygen and air. When the epoxidation uses hydrogen peroxide or oxone ($2KHSO_5 \cdot KHSO_4 \cdot K_2SO_4$) as an oxidizing agent, the system is preferably buffered by ammonium bicarbonate or sodium bicarbonate.

Typically, the epoxidation is effected at a temperature ranging from about 0° C. to 60° C.

The present invention was developed by first conducting an epoxidation of $Si^tBu(CH_3)_2$ protected cyclohexen-1-ol 3c using [Mn(TDCPP)Cl] (1) as catalyst and environmentally benign hydrogen peroxide ($H_2O_2$) as oxidant. Manganese porphyrins are known to be effective catalysts for epoxidation of simple alkenes using $H_2O_2$ [see for examples: Battioni, P.; Renaud, J. P.; Bartoli, J. F.; Reina-Artiles, M.; Fort, M.; Mansuy, D *J. Am. Chem. Soc.* 1988, 110, 8462. Battioni, P.; Mansuy, D. *J. Chem. Soc., Chem., Commun.* 1994, 1035. Poriel, C.; Ferrand, Y.; Le Maux, P.; Rault-Berthelot, J.; Simonneaux, G. *Tetrahedron Lett.* 2003, 44, 1759]. Treatment of a $CH_3CN$ solution of 3c and 1 (1.2 mol %) with a solution of 35% $H_2O_2$ in aqueous $NH_4HCO_3/CH_3CN$ afforded trans- and cis-epoxides 4c in 88% isolated yield. On the basis of capillary GC analysis, the trans-selectivity (i.e., trans-:cis-epoxide ratio) was determined to be 33:1 (Table 1, entry 3). For $MnSO_4$ salt catalyzed alkene epoxidation using bicarbonate-activated $H_2O_2$, see: Burgess, K.; Lane, B. S. *J. Am. Chem. Soc.* 2001, 123, 2933. Lane, B. S.; Vogt, M.; DeRose, V. J.; Burgess, K. *J. Am. Chem. Soc.* 2002, 124, 11946.

TABLE 1

Diastereoselective Epoxidation of Cycloalkenes 3a-3n by 1 Using $H_2O_2$[a]

| entry | alkene | | $R_1$ | $R_2$ | % yield of epoxide[b] | trans-:cis-epoxide ratio[c] | |
|---|---|---|---|---|---|---|---|
| | | | | | | 1 | m-CPBA[d] |
| 1 | | 3a | OH | H | 59[e] | 4:1 | 1:7 |
| 2 | | 3b | OAc | H | 71 | 5:1 | 2:1 |
| 3 | | 3c | $OSi^tBu(CH_3)_2$ | H | 88 | 33:1[e] | 5:1 |
| 4 | | 3d | $OSi^tBu(Ph)_2$ | H | 64[f] | 16:1 | 4:1 |
| 5 | | 3e | OH | $CH_3$ | 52[c,g] | 9:1 | 1:10 |
| 6 | | 3f | OAc | $CH_3$ | 69[h,f] | 9:1 | 3:1 |
| 7 | | 3g | $OSi^tBu(CH_3)_2$ | $CH_3$ | 80[f] | 11:1 | 8:1 |
| 8 | | 3h | $OSi^tBu(Ph)_2$ | $CH_3$ | 57[i,f] | 35:1 | 3:1 |
| 9 | | 3i | COOMe | H | 97[e] | 30:1 | 1:1 |
| 10 | | 3j | $COOC_6H_{11}$ | H | 92[e] | | 1:1 |
| 11 | | 3k | $COOCH(Ph)_2$ | H | 74 | | 1:1 |
| 12 | | 3l | $N(Boc)_2$ | H | 90[e] | | n.d.[j] |
| 13 | | 3m | $OSi^tBu(CH_3)_2$ | — | 82[e] | 18:1 | 1:1 |
| 14 | | 3n | $OCH_2Ph$ | — | 83[e] | | 2:1 |

[a]Unless otherwise indicated, all the epoxidation reactions were performed as follows: A solution of alkene (0.25 mmol) and 1 (3 μmol) in $CH_3CN$ (4 mL) was added a pre-mixed solution of 0.8 M aqueous $NH_4HCO_3$ (0.5 mL), $CH_3CN$ (0.5 mL) and 35% $H_2O_2$ (0.125 mL) at room temperature.
[b]Isolated yield based on complete alkene consumption, and <5% of enone was formed based on $^1H$ NMR analysis.
[c]Determined by $^1H$ NMR.
[d]Epoxidations were carried out in $CH_2Cl_2$ for 3 h with a alkene:m-CPBA:$NaHCO_3$ molar ratio of 1:1.5:3.
[e]Determined by GC.
[f]7-15% of enone was formed based on $^1H$ NMR analysis.
[g]10% of 3-methyl-2-cyclohexenone was detected by $^1H$ NMR.
[h]Isolated yield based on 87% alkene conversion.
[i]Isolated yield based on 84% alkene conversion.
[j]No epoxide was detected.

The activities of other manganese porphyrin catalysts for the diastereoselective epoxidation of 3c were examined under the same reaction conditions. It was found that [Mn(TDCPP)Cl] (1) exhibits the best catalytic activity (88% epoxide yield) and trans-selectivity (33:1). With [Mn(TMP)Cl](3) as catalyst, trans-selectivity of 22:1 and epoxide yield of 56% (based on 16% conversion) were observed. While [Mn(TTP)Cl](5) was found to exhibit poor catalytic activity (<5% conversion), the perfluorinated analog (i.e., [Mn(TFPP)Cl])(4) gave trans-selectivity of 12:1 with modest catalytic activity (61% yield based on 25% conversion). It should be noted that all the metalloporphyrin catalysts exhibited higher trans-selectivity than m-CPBA.

With these promising data in hand, other substrates have been examined by using 1 as catalyst. The catalytic oxidation of 3g ($R_1$=OSi$^t$Bu(CH$_3$)$_2$, $R_2$=CH$_3$) proceeded with 80% epoxide formation and trans-selectivity >99:1 (Table 1, entry 7). It is known that m-CPBA and dioxiranes are common oxidants for alkene epoxidation. It was found that 3c and 3g reacted with m-CPBA to give trans-4c and trans-4g with trans-selectivities of 5:1 and 8:1, respectively. According to the literature, the trans-selectivities obtained in dioxirane mediated epoxidation of 3c and 3g are 13:1 [Miyata, N.; Kurihara, M.; Ito, S.; Tsutsumi, N. *Tetrahedron Lett.* 1994, 35, 1577] and 20:1 [Yang, D.; Jiao, G.-S.; Yip, Y.-C.; Wong, M.-K. *J. Org. Chem.* 1999, 64, 1635], respectively. To our knowledge, the trans-selectivity for the 1-catalyzed epoxidation of 3c and 3g are the best results ever achieved.

The trans-selectivity was found to be dependent upon the size of the substituents $R_1$ and $R_2$. While the 1-catalyzed epoxidation of 3c ($R_1$=OSi$^t$Bu(CH$_3$)$_2$, $R_2$=H) proceeded with excellent trans-selectivity (trans:cis=33:1), the related reactions with 3a ($R_1$=OH, $R_2$=H) and 3b ($R_1$=OAc, $R_2$=H) were found to exhibit lower diastereoselectivity (trans:cis~5:1). When 3d ($R_1$=OSi$^t$Bu(Ph)$_2$, $R_2$=H) was employed as substrate, the 1-catalyzed reaction attained a lower diastereoselectivity (16:1) compared to the value for the related reaction of 3c. Similar dependence on substituent was also encountered for the catalytic epoxidation of 3e-h. Interestingly, the trans-selectivities obtained in the epoxidation of 3e-h with $R_2$=CH$_3$ were significantly higher than that of 3a-d with $R_2$=H. It should be noted that in all cases trans-epoxides were obtained selectively in moderate to good yields with much better trans-selectivity than the m-CPBA-mediated reactions.

With 1 as catalyst, catalytic epoxidation of allylic esters and amines were also performed. As shown in Table 1, trans-selectivity of 35:1 was attained for the epoxidation of 3k ($R_1$=COOCH(Ph)$_2$, $R_2$=H). However, with m-CPBA as oxidant, only equimolar mixtures of trans-/cis-epoxides were obtained for the oxidation of 3i-k. Amine 3l ($R_1$=N(Boc)$_2$, $R_2$=H) can be readily converted to its trans-epoxide selectively (trans:cis=30:1) under the 1-catalyzed conditions. For 1-catalyzed epoxidation of cyclopenten-1-ols 3m ($R_1$=OSi$^t$Bu(CH$_3$)$_2$) and 3n ($R_1$=OCH$_2$Ph), trans-selectivities of 18:1 and 10:1 were attained, respectively.

In addition, the catalytic activity of [Ru(TDCPP)CO] (2) for epoxidation allylically substituted cylcohexenes was also examined (Table 2). The 2-catalyzed epoxidation of 3a furnished cis-epoxide as major product (trans:cis=1:5). Assuming a metal-oxo intermediate, the observed cis-selectivity is probably due to the hydrogen bonding effect of the syn-directing OH group in CH$_2$Cl$_2$. Compared to 1, 2 was found to afford much higher trans-selectivities in the catalytic expoxidation of 3c (>99:1), 3i (8:1), and 3m (71:1). Interestingly, under the 2-catalyzed epoxidation conditions, enone 3o was converted to trans-epoxide exclusively, while the analogous reaction of enone 3p gave the corresponding trans-epoxide as major product (trans:cis=44:1). It is worthy to note that high product turnover number up to 3,000 could be achieved for the 2-catalyzed epoxidation of 3p without compromise on the trans-selectivity.

TABLE 2

Diastereoselective Epoxidation of Cycloalkenes by 2 Using 2,6-Dichloropyridine N-oxide[a]

| entry | alkene | % conv.[b] | % yield of epoxide[b] | trans-:cis-epoxide ratio[b] |
|---|---|---|---|---|
| 1 | 3a | 92 | 86 | 1:5 |
| 2 | 3c | 100 | 85 | >99:1 |
| 3 | 3i | 97 | 65 | 8:1 |
| 4 | 3m | 100 | 99 | 71:1 |
| 5 | 3o (OSi$^t$Bu(CH$_3$)$_2$) | 91 | 85 | trans only |
| 6 | 3p (OSi$^t$Bu(CH$_3$)$_2$) | 94 | 85 | 44:1 |

[a]All the epoxidation reactions were carried out in CH$_2$Cl$_2$ at 40° C. for 48 h with a 2:2,6-Cl$_2$pyNO:alkene molar ratio of 1:150:100 under nitrogen atmosphere.
[b]Determined by $^1$H NMR with internal standard.

Apart from cyclic allylic alkenes, diastereoselective epoxidation of acyclic allylically substituted alkene 5a using 2,6-dichloropyridine-N-oxide was also examined.

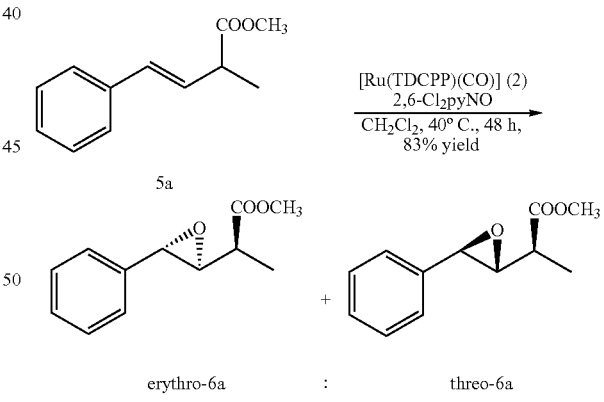

Under the 2-catalyzed epoxidation conditions, erythro-epoxide 6a was obtained as the major product (erythro-6a:threo-6a=5:1) in high yield. This erythro-selectivity is higher than the m-CPBA mediated epoxidation of 5a (erythro-6a:threo-6a=1.6:1). In addition, using 1 as catalyst and oxone as oxidant, 6a (erythro:threo=6:1) was obtained in 70% yield based on 93% conversion.

As the steric bulky metalloporphyrin catalysts exhibited high diastereoselectivity in epoxidation of allylic alkenes, attention was directed to the activity of 1 in epoxidation of allylic terminal alkenes. Using the "1+Oxone" approach, terminal allylic alcohol 7a could be epoxidized to 8a with erythro-selectivity of 5.7:1 (see Table 3 below, entry 1), and higher erthyro-selectivity (7.8:1) could be achieved with $H_2O_2$ as terminal oxidant (entry 2). For a bulkier allylic alcohol 7b, epoxide 8b with erythro-selectivities of 7:1 and 9:1 could be obtained in the 1-catalyzed epoxidations with oxone and $H_2O_2$ as oxidant, respectively (entries 3 and 4). Notice that m-CPBA could only give 1:1 mixtures of erythro- and threo-epoxides 8a and 8b. To the best of our knowledge, the erythro-selectivities for the 1-catalyzed epoxidations of 7a and 7b are the best results ever achieved [cf. Kurihara, M.; Ishii, K.; Kasahara,Y.; Kameda, M.; Pathak, A. K.; Miyata, N. Chem. Lett. 1997, 1015].

Diastereoselective epoxidation reactions of other classes of terminal alkenes were also examined. A search of literature revealed that some erythro-amino epoxides are key building blocks for the synthesis of several FDA-approved anti-HIV drugs [Ghosh, A. K.; Bilcer, G.; Schiltz, G. Synthesis 2001, 15, 2203]. Particularly, phenylalanine derived erythro-amino epoxides have been used as the key synthetic intermediates for the construction of saquinavir and amprenavir. Currently, these erythro-epoxides could be obtained by ring-closure reactions of β-halohydrins [Rotella, D. P. Tetrahedron Lett. 1995, 36, 5453. Albeck, A.; Estreicher, G. I. Tetrahedron 1997, 54, 5325. Kim, B. M.; Bae, S. J.; So, S. M.; Yoo, H. T.; Chang, S. K.; Lee, J. H.; Kang, J. Org. Lett. 2001, 3, 2349. Wang, D.; Schwinden, M. D.; Radesca, L.; Patel, B.; Kronenthal, D.; Huang, M.-H.; Nugent, W. A. J. Org. Chem. 2004, 69, 1629], and other methods [Parkes, K. E. B.; Bushnell, D. J.; Crackett, P. H.; Dunsdon, S. J.; Freeman, A. C.; Gunn, M. P.; Hopkins, R. A.; Lambert, R. W.; Martin, J. A. et al. J. Org. Chem. 1994, 59, 3656. Branalt, J.; Kvarnstrom, I.; Classon, B.; Samuelsson, B.; Nillroth, U.; Danielson, U. H.; Karlen, A.; Hallberg, A. Tetrahedron Lett. 1997, 38, 3483. Aguilar, N.; Moyano, A.; Pericas, M. A.; Riera, A. J. Org. Chem. 1998, 63, 3560. Kurihara, M.; Ishii, K.; Kasahara,Y.; Miyata, N. Tetrahedron Lett. 1999, 40, 3183]. However, m-CPBA epoxidation could only afford threo-major epoxides [Luly, J. R.; Dellaria, J. F.; Plattner, J. J.; Soderquist, J. L.;Yi, N. J. Org. Chem. 1987, 52, 1487. Jenmalm, A.; Berts, W.; Li,Y.-L.; Luthman, K.; Csoeregh, I.; Hacksell, U. J. Org. Chem. 1994, 59, 1139. Romeo, S.; Rich, D. H. Tetrahedron Lett. 1994, 35, 4939]. Before the present invention, there is no direct epoxidation available to access these erythro-major amino epoxides.

As illustrated in Table 3, the "1+oxone" oxidation system could achieve erythro-selective epoxidation of phthalimide-protected allylic amines 7c-e and Boc-protected allylic amine 7f in high yields. For epoxidation of 7c bearing a benzyl group, epoxide 8c with erythro-selectivity of 3.4:1 in 96% isolated yield based on 88% conversion could be achieved while m-CPBA provided threo-major epoxide 8c with selectivity of 1:3. This is the first example in which erythro-major 8c can be obtained via direct epoxidation of 7c. By conducting the epoxidation at 0° C., erythro-selectivity of 3.6:1 could be attained (Table 3, entry 6). For epoxidation of 7d with an isopropyl group, an increase in erythro-selectivity to 5:1 was observed (entry 7), indicating that this epoxidation is sensitive to the steric bulkiness of the α-substituent. For 7e and Boc-protected 7f, erythro-selectivities of 1.8:1 and 1.4:1 were observed, respectively (entries 8 and 9). It should be noted that m-CPBA gave threo-major epoxides in the epoxidation of 7d (1:3), 7e (1:4) and 7f (1:13).

TABLE 3

Epoxidation of Allylic Terminal Alkenes 7 by Mn-porphyrins[a]

| Entry | Alkene | | % Conv.[b] | % yield[b] | 1 | m-CPBA[c] |
|---|---|---|---|---|---|---|
| 1 | $OSi^tBu(CH_3)_2$ | 7a | 100 | 35 | 5.7:1 | 1:1 |
| 2[d] | | | | 93 | 62 | 7.8:1 | |
| 3 | $OSi^tBu(CH_3)_2$, $C_3H_7$ | 7b | 100 | 61 | 7:1 | 1:1 |
| 4[d] | | | | 77 | 78 | 9:1 | |

TABLE 3-continued

Epoxidation of Allylic Terminal Alkenes 7 by Mn-porphyrins[a]

$$\underset{7}{\overset{X}{\underset{Y}{\diagup}}} \xrightarrow[CH_3CN/H_2O, RT]{1/NH_4OAc/oxone/NH_4HCO_3}$$

X = O, N
Y = alkyl erythro-8  :  thero-8

| Entry | Alkene | | % Conv.[b] | % yield[b] | E:T - epoxide ratio[b] 1 | m-CPBA[c] |
|---|---|---|---|---|---|---|
| 5 | (phthalimide-CH2-CH(allyl)-CH2-Ph) | 7c | 88 | 93(96)[e] | 3.4:1 | 1:3 |
| 6[f] | | | 80 | 91 | 3.6:1 | |
| 7 | (phthalimide-N-CH(allyl)-iPr) | 7d | 86 | 87 | 5:1 | 1:3 |
| 8 | (phthalimide-N-CH(allyl)-CH2-iPr) | 7e | 85 | 82 | 1.8:1 | 1:4 |
| 9 | (BocNH-CH(allyl)-CH2-Ph) | 7f | 89 | 88 | 1.4:1 | 1:13 |

[a] Unless otherwise indicated, all the epoxidation reactions were performed as follows: Alkene (0.1 mmol), NH$_4$OAc (0.05 mmol) and catalyst (0.5 μmol) in CH$_3$CN solution was added Oxone (0.13 mmol) and NH$_4$HCO$_3$ (0.4 mmol) at room temperature for 1 h.
[b] Determined by $^1$H NMR.
[c] Epoxidations were carried out in CH$_2$Cl$_2$ with an alkene/m-CPBA/NaHCO$_3$ molar ratio of 1:2:3.
[d] To a solution of alkene (0.2 mmol), NH$_4$OAc (0.03 mmol) and 1 (2 μmol) in CH$_3$CN (4 ml) was added a premixed solution of NH$_4$HCO$_3$ (0.6 mmol), CH$_3$CN (0.5 ml), H$_2$O (0.5 ml) and 35% H$_2$O$_2$ (0.1 ml) at room temperature (Reaction time: 2 h).
[e] Isolated yield based on 88% conversion.
[f] At 0° C. for 5 h.

In summary, general and efficient methods for highly trans-selective epoxidation of allylically substituted alkenes by sterically bulky metallo-porphyrin catalysts have been developed. These methods offer an easy assess to a diversity of synthetically useful trans-epoxides.

EXAMPLE 1

A direct method of synthesis of trans-selective epoxide using manganese porphyrin (1) as catalyst and $H_2O_2$ as oxidant is as follows. To a round-bottom flask containing [Mn(TDCPP)Cl] (1) (3.0 mg, 0.003 mmol) and 3c (53.0 mg, 0.25 mmol) in $CH_3CN$ (4 mL) was added a premixed solution of 35% $H_2O_2$ (0.125 mL), aqueous $NH_4HCO_3$ (0.8 M, 0.5 mL) and $CH_3CN$ (0.5 mL) via a syringe pump for 1.5 h at room temperature. After being stirred for 1 h, the reaction mixture was diluted with saturated aqueous $Na_2S_2O_3$ (1 mL) and extracted with n-hexane (4×20 mL). The combined organic layers were dried over anhydrous $MgSO_4$, filtered through a short pad of silica gel, and concentrated under reduced pressure. The ratio of trans-4c to cis-4c was determined to be 33:1 by capillary GC analysis. The residue was purified by flash column chromatography (5% EtOAc in n-hexane) to provide a mixture of epoxides trans-4c and cis-4c (49 mg, 88% yield based on complete alkene conversion) as a colorless oil.

EXAMPLE 2

Direct method of synthesis of trans-selective epoxide using ruthenium porphyrin (2) as catalyst and 2,6-$Cl_2$pyNO as oxidant: To a dried $CH_2Cl_2$ solution (4 mL) containing 3c (53.0 mg, 0.25 mmol) was added [Ru(TDCPP)(CO)(MeOH)] (2) (2.6 mg, 0.0025 mmol) and 2,6-$Cl_2$pyNO (61.5 mg, 0.38 mmol) under an nitrogen atmosphere. After stirring at 40° C. for 48 h, the reaction mixture was concentrated under reduced pressure. The residue was added 4-bromochlorobenzene as an internal standard, and the organic products were then analyzed and quantified by $^1$H NMR spectroscopy. The ratio of trans-4c:cis-4c was determined to be >99:1 by $^1$H NMR. The yield of epoxides trans-4c and cis-4c was 85% based on complete alkene conversion.

The spectral data of cycloalkenes 3b-3d, 3f-3g, 3i, and 3l-3p are identical with those reported in the following literature:

| | |
|---|---|
| 3b, 3f | Pearson, A. J.; Hsu, S.-Y. J. Org. Chem. 1986, 51, 2505. |
| 3c, 3g | Corey, E. J.; Venkateswarlu, A. J. Am. Chem. Soc. 1972, 94, 6190. |
| 3d | Detty, M. R.; Seidler, M. D. J. Org. Chem. 1981, 46, 1283. |
| 3i | Davies, S. G.; Whitham, G. H. J. Chem. Soc. Perkin Trans. 1 1976, 2279. |
| 3l | van Benthem, Rolf A. T. M.; Michels, J. J.; Hiemstra, H.; Nico Speckamp, W. Synlett. 1994, 368. |
| 3m | Ahn, D.-R.; Mosimann, M.; Leumann, C. J. J. Org. Chem. 2003, 68, 7693. |
| 3n | Crotti, P.; Di Bussolo, V.; Favero, L.; Macchia, F.; Pineschi, M. Eur. J. Org. Chem. 1998, 1675. |
| 3o | Tachihara, T.; Kitahara, T. Tetrahedron 2003, 59, 1773. |
| 3p | Curran, T. T.; Hay, D. A.; Koegel, C. P. Tetrahedron 1997, 53, 1983. |

The spectral data of epoxides 4a-4g, 4i and 4m-4p are identical with those reported in the literature.

| | |
|---|---|
| 4a, 4b, 4e, 4f, and 4i | Murray, R. W.; Singh, M.; Williams, B. L.; Moncrieff, H. M. J. Org. Chem. 1996, 61, 1830. |
| 4c | Kurihara, M.; Ito, S.; Tsutsumi, N.; Miyata, N. Tetrahedron Lett. 1994, 35. 1577. |
| 4d | Demay, S.; Kotschy, A.; Knochel, P. Synthesis 2001, 863. |
| 4g | Yang, D.; Jiao, G.-S.; Yip, Y.-C.; Wong, M.-K. J. Org. Chem. 1999, 64, 1635. |
| 4m | Ahn, D.-R.; Mosimann, M.; Leumann, C. J. J. Org. Chem. 2003, 68, 7693. |
| 4n | Crotti, P.; Di Bussolo, V.; Favero, L.; Macchia, F.; Pineschi, M. Eur. J. Org. Chem. 1998, 1675. |
| 4o | Tachihara, T.; Kitahara, T. Tetrahedron 2003, 59, 1773. |
| 4p | trans-4p: Tanaka, H.; Yamada, H.; Matsuda, A.; Takahashi, T. Synlett. 1997, 381. cis-4p: Theil, F. Tetrahedron: Asymmetry 1995, 6, 1693. |

Preparation Procedures and Characterization Data of Cycloalkenes 3h, 3j and 3k

3h

A solution of 3-methyl-2-cyclohexen-1-ol (0.49 g, 5 mmol), TBDPSCl (1.01 g, 5.5 mmol), imidazole (0.5 g, 7.3 mmol) in anhydrous DMF (5 mL) was stirred at room temperature for 16 h. The mixture was diluted with EtOAc (50 mL), washed with 1 N HCl, saturated $NaHCO_3$ solution and brine, and concentrated under reduced pressure. The residue was purified by flash column chromatography (1% EtOAc in hexane) to afford alkene 3h (1.4 g, 4.0 mmol, 80% yield). Colorless oil, analytical TLC (silica gel 60) (10% EA in hexane), $R_f$=0.58; $^1$H NMR (400 MHz, $CDCl_3$) δ 7.70-7.68 (m, 4H), 7.43-7.24 (m, 6H), 5.35 (s, 1H), 4.21 (br s, 1H), 1.94-1.79 (m, 1H), 1.78-1.72 (m, 2H), 1.61 (s, 3H), 1.60-1.53 (m, 2H), 1.46-1.37 (m, 1H), 1.06 (s, 9H); $^{13}$C NMR (75.47 MHz, $CDCl_3$) δ 136.91, 135.87, 135.82, 134.79, 134.73, 129.41, 129.39, 127.44, 127.42, 125.32, 67.83, 31.93, 30.01, 27.05, 23.59, 19.58, 19.20; IR (KBr) 2931, 1472, 821 $cm^{-1}$; EIMS m/z 360 ($M^+$), 298 ($M^+$-$tC_4H_9$); HRMS (EI) for $C_{23}H_{30}OSi$, calcd 360.2066, found 360.2062.

3j

A solution of cyclohex-2-enecarboxylic acid (0.4 g, 3.2 mmol), cyclohexanol (0.635 g, 6.4 mmol), DMAP (0.195 g, 1.6 mmol), EDCI (0.92 g, 4.8 mmol) in anhydrous $CH_2Cl_2$ (10 mL) were stirred at room temperature for 6 h. The reaction mixture was diluted with $CH_2Cl_2$ (70 mL), washed with $H_2O$ (2×10 mL), and dried over anhydrous $Na_2SO_4$. The reaction mixture was filtered, and concentrated under reduced pressure. The residue was purified by flash column chromatography (3% EtOAc in hexane) to afford alkene 3j (0.5 g, 2.4 mmol, 75% yield). Colorless oil, analytical TLC (silica gel 60) (10% EA in hexane), $R_f$=0.50; $^1$H NMR (300 MHz, $CDCl_3$) δ 5.85-5.74 (m, 2H), 4.81-4.77 (m, 1H), 3.06 (m, 1H), 2.02 (m, 2H), 1.92-1.64 (m, 7H), 1.60-1.26 (m, 7H); $^{13}$C NMR (75.47 MHz, $CDCl_3$) δ 174.00, 129.36, 124.65, 72.36, 41.39, 31.51, 25.43, 25.32, 24.67, 23.59, 20.80; IR (KBr) 1722 $cm^{-1}$; EIMS m/z 208 ($M^+$); HRMS (EI) for $C_{13}H_{20}O_2$, calcd 208.1463, found 208.1443. (Synthesis of cyclohex-2-enecarboxylic acid, see: Davies, S. G.; Whitham, G. H. J. Chem. Soc. Perkin Trans. 1 1976, 2279.)

3k

A solution of cyclohex-2-enecarboxylic acid (0.48 g, 3.8 mmol), benzhydrol (1.4 g, 7.6 mmol), DMAP (0.23 g, 1.9 mmol), EDCI (1.1 mg, 5.7 mmol) and anhydrous $CH_2Cl_2$ (10 mL) were stirred at room temperature for 6 h. The reaction mixture was diluted with $CH_2Cl_2$ (70 mL), washed with $H_2O$ (2×10 mL), and over anhydrous $Na_2SO_4$. The reaction mixture was filtered, and concentrated under reduced pressure. The residue was purified by flash column chromatography (3% EtOAc in hexane) to afford alkene 3k (0.77 g, 2.6 mmol, 69% yield). Colorless oil, analytical TLC (silica gel 60) (10%

EA in hexane), $R_f$=0.58; $^1$H NMR (300 MHz, CDCl$_3$) δ 7.34-7.26 (m, 10H), 6.88 (s, 1H), 5.86-5.83 (m, 2H), 3.22-3.20 (m, 1H), 2.04-1.75 (m, 5H), 1.63-1.56 (m, 1H); $^{13}$C NMR (75.47 MHz, CDCl$_3$) δ 173.77, 140.85, 140.80, 130.25, 128.91, 128.26, 128.24, 127.49, 127.42, 124.50, 77.20, 41.72, 25.67, 25.07, 21.18; IR (KBr) 1715 cm$^{-1}$; EIMS m/z 292 (M$^+$), 167 (M$^+$-C$_7$H$_9$O$_2$); HRMS (EI) for C$_{20}$H$_{20}$O$_2$, calcd 292.1463, found 292.1455.

Characterization Data of Epoxides 4h, and 4j-4l

A Mixture of trans-4h and cis-4h

Colorless oil, analytical TLC (silica gel 60) (10% EA in hexane), trans-4h $R_f$=0.28, cis-4h $R_f$=0.25; $^1$H NMR (400 MHz, CDCl$_3$) δ 7.96-7.66 (m, 4H), 7.45-7.34 (m, 6H), 4.02-3.96 (m, 1H), 2.93 (br s, 4/5×1H), 2.87 (br s, 1/5×1H), 1.85-1.35 (m, 5H), 1.29 (s, 4/5×3H), 1.26-1.13 (m, 1H), 1.22 (s, 1/5×3H), 1.09 (s, 4/5×9H), 1.08 (s, 1/5×9H); $^{13}$C NMR (100.61 MHz, CDCl$_3$) δ 135.78, 135.70, 134.04, 133.86, 129.68, 129.65, 129.56, 127.62, 127.55, 127.52, 29.96, 29.39, 28.04, 27.66, 26.95, 26.89, 24.05, 23.36, 19.70, 19.17, 15.68; IR (KBr) 2933, 1472, 822 cm$^{-1}$; EIMS m/z 366 (M$^+$), 309 (M$^+$-tC$_4$H$_9$); HRMS (EI) for C$_{23}$H$_{30}$O$_2$Si, calcd 366.2015, found 366.2015.

trans-4j

Colorless oil, analytical TLC (silica gel 60) (10% EA in hexane), $R_f$=0.31; $^1$H NMR (400 MHz, CDCl$_3$) δ 4.86-4.80 (m, 1H), 3.41 (d, J=3.9 Hz, 1H), 3.22-3.20 (m, 1H), 2.87-2.84 (dd, J=8.6, 5.6 Hz, 1H), 2.08-2.03 (m, 1H), 1.85-1.69 (m, 6H), 1.57-1.25 (m, 9H); $^{13}$C NMR (100.62 MHz, CDCl$_3$) δ 172.97, 72.80, 52.36, 52.24, 40.91, 31.49, 31.43, 25.32, 23.94, 23.78, 23.55, 23.53, 16.80; IR (KBr) 1728 cm$^{-1}$; EIMS m/z 224 (M$^+$); HRMS (EI) for C$_{13}$H$_{20}$O$_3$, calcd 224.1412, found 224.14037.

cis-4j

Colorless oil, analytical TLC (silica gel 60) (10% EA in hexane), $R_f$=0.25; $^1$H NMR (400 MHz, CDCl$_3$) δ 4.88-4.84 (m, 1H), 3.45 (t, J=3.5 Hz, 1H), 3.21-3.19 (m, 1H), 2.83-2.78 (m, 1H), 1.90-1.82 (m, 4H), 1.76-1.67 (m, 3H), 1.61-1.23 (m, 9H); $^{13}$C NMR (100.62 MHz, CDCl$_3$) δ 172.24, 72.75, 52.26, 52.18, 41.13, 31.50, 31.47, 25.40, 23.53, 23.58, 23.35, 21.29, 18.91; IR (KBr) 1734 cm$^{-1}$; EIMS m/z 125 (M$^+$-C$_6$H$_{11}$O); HRMS (EI) for C$_7$H$_9$O$_2$, calcd 125.0603, found 125.0602.

trans-4k

Colorless oil, analytical TLC (silica gel 60) (20% EA in hexane), $R_f$=0.38; $^1$H NMR (300 MHz, CDCl$_3$) δ 7.35-7.26 (m, 10H), 6.92 (s, 1H), 3.45 (d, 3.5 Hz, 1H), 3.21-3.19 (m, 1H), 3.01 (dd, J=8.8, 6.5 Hz, 1H), 2.08-2.01 (m, 1H), 1.91-1.87 (m, 1H), 1.86-1.70 (m, 1H), 1.49-1.33 (m, 3H); $^{13}$C NMR (75.47 MHz, CDCl$_3$) δ 172.85, 140.44, 140.37, 128.97, 128.95, 128.43, 128.38, 127.46, 127.36, 77.60, 52.65, 52.56, 41.26, 24.29, 24.12, 17.17; IR (KBr) 1732 cm$^{-1}$; EIMS m/z 308 (M$^+$), 183 (M$^+$-C$_7$H$_9$O$_2$); HRMS (EI) for C$_{20}$H$_{20}$O$_3$, calcd 308.1412, found 308.1407.

cis-4k

Colorless oil, analytical TLC (silica gel 60) (20% EA in hexane), $R_f$=0.30; $^1$H NMR (300 MHz, CDCl$_3$) δ 7.39-7.23 (m, 10H), 6.94 (s, 1H), 3.54 (t, J=3.4 Hz, 1H), 3.24-3.21 (m, 1H), 2.95-2.89 (m, 1H), 1.91-1.85 (m, 2H), 1.80-1.64 (m, 1H), 1.61-1.57 (m, 2H), 1.29-1.22 (m, 1H); $^{13}$C NMR (75.47 MHz, CDCl$_3$) δ 171.79, 140.20, 140.13, 128.44, 128.40, 127.87, 127.71, 127.20, 126.82, 77.14, 52.12, 51.95, 41.27, 23.23, 21.32, 18.90; IR (KBr) 1738 cm$^{-1}$; EIMS m/z 308 (M$^+$), 183 (M$^+$-C$_7$H$_9$O$_2$); HRMS (EI) for C$_{20}$H$_{20}$O$_3$, calcd 308.1412, found 308.1405.

trans-4l

Colorless oil; analytical TLC (silica gel 60) (30% EA in hexane), $R_f$=0.67; $^1$H NMR (300 MHz, CDCl$_3$) δ 4.32 (dd, J=10.8, 6.3 Hz, 1H), 3.29 (m, 1H), 3.22 (d, J=3.9 Hz, 1H), 2.12-2.07 (m, 1H), 1.79-1.68 (m, 2H), 1.52 (s, 18H), 1.48-1.43 (m, 2H), 1.42-1.26 (m, 1H); $^{13}$C NMR (75.47 MHz, CDCl$_3$) δ 152.97, 83.31, 57.54, 54.18, 53.25, 28.57, 25.90, 24.68, 16.81; IR (KBr) 1738, 1698 cm$^{-1}$; EIMS m/z 257 (M$^+$+1-tC$_4$H$_9$); HRMS (EI) for C$_{12}$H$_{19}$O$_5$N (M$^+$+1-C$_4$H$_9$), calcd 257.1263, found 257.1261.

EXAMPLE 3

A direct method of synthesis of erythro-selective epoxide using [Ru(TDCPP)CO] (2) as catalyst and 2,6-Cl$_2$pyNO as oxidant is as follows. To a dried CH$_2$Cl$_2$ solution (3 mL) containing 5a (0.2 mmol) were added [Ru(TDCPP)CO] (2) (2 μmol) and 2,6-Cl$_2$pyNO (0.26 mmol) under nitrogen atmosphere. After being stirred at 40° C. for 48 h, the reaction mixture was concentrated under reduced pressure. To the residue was added 1,1-diphenyl ethylene as an internal standard, and the organic products were analyzed and quantified by $^1$H NMR spectroscopy. The ratio of epoxides erythro-6a/threo-6a was determined to be 5:1 by $^1$H NMR. The combined yield of erythro-6a and threo-6a was 83% based on 82% alkene conversion.

EXAMPLE 4

A direct method of synthesis of erythro-selective epoxide using [Mn(TDCPP)Cl] (1) as catalyst and oxone as oxidant is as follows. To a round-bottom flask containing [Mn(TDCPP)Cl] (1) (0.5 μmol), 5a (0.1 mmol) and ammonium acetate (0.05 mmol) in a solution of CH$_3$CN (3 mL) and H$_2$O (2 mL) was added a mixture of Oxone (0.13 mmol) and ammonium bicarbonate (0.4 mmol). After stirring at room temperature for 2 h, the reaction mixture was diluted with saturated aqueous Na$_2$S$_2$O$_3$ solution (1 mL), and extracted with n-hexane (4×20 mL). The combined organic layers were dried over anhydrous Na$_2$SO$_4$, filtered, and concentrated under reduced pressure. To the residue was added 1,1-diphenyl ethylene as an internal standard, and the organic products were analyzed and quantified by $^1$H NMR spectroscopy. The ratio of epoxides erythro-6a/threo-6a was determined to be 6:1 by $^1$H NMR. The combined yield of erythro-6a and threo-6a was 70% based on 93% alkene conversion.

EXAMPLE 5

A direct method of synthesis of erythro-selective epoxide using [Mn(TDCPP)Cl] (1) as catalyst and oxone as oxidant is as follows. To a round-bottom flask containing [Mn(TDCPP)Cl] (1) (0.5 μmol), 7c (0.1 mmol) and ammonium acetate (0.05 mmol) in a solution of CH$_3$CN (3 mL) and H$_2$O (2 mL) was added a mixture of oxone (0.13 mmol) and ammonium bicarbonate (0.4 mmol). After stirring at room temperature for 1 h, the reaction mixture was diluted with saturated aqueous Na$_2$S$_2$O$_3$ solution (1 mL), and extracted with n-hexane (4×20 mL). The combined organic layers were dried over anhydrous Na$_2$SO$_4$, filtered, and concentrated under reduced pressure. The residue was added 4-bromochlorobenzene as an internal standard, and the organic products were analyzed and quantified by $^1$H NMR spectroscopy. The ratio of epoxides erythro-8c/threo-8c was determined to be 3.4:1 by $^1$H NMR. The combined yield of erythro-8c and threo-8c was 93% based on 88% alkene conversion. The residue was purified by flash column chromatography (20% EtOAc in hexane)

to provide a mixture of epoxides erythro-8c and threo-8c (24.7 mg, 96% yield based on 88% conversion) as a solid.

Various changes and modification can be made in the present invention without departing from the spirit and scope thereof. The various embodiments described herein were for the purpose of illustration only and were not intended to limit the invention.

What is claimed is:

1. A method for synthesizing a trans-/erythro-epoxide from an allylically substituted alkene comprising the step of catalyzing the reaction of a bicarbonate activated hydrogen peroxide oxidant and derivatives thereof and the allylically substituted alkene with a catalytic amount of a manganese metalloporphyrin as the catalyst for producing the epoxide, wherein the alkene has the formula R—CH($R_1$)—CH=CH—CH—R in which each of the carbon atoms is optionally substituted and two R groups can be linked to form with the carbon atoms to which they are attached, a 5-, 6-, 7-, 8- or 9-membered ring, which itself can be fused to another ring, and $R_1$ is a halogen, heteroatom, hydroxyl, alkoxy, substituted hydroxy, carboxyl, carbonyl, cyano, silyl, boro, phosphorus containing, sulfur containing, amino, substituted amino, nitro, alkyl, substituted alkyl, aryl, substituted aryl, heteroaryl, or substituted heteroaryl group allylic substituent.

2. The method of claim 1, wherein the manganese metalloporphyrin is a metal complex of the formula (I):

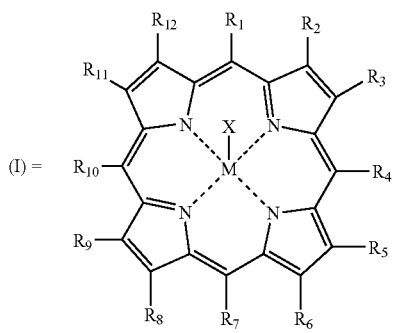

wherein X is selected from Cl, CO, O2-(oxO), N3-(nitrido), NR(imide) (where R=alkyl, aryl, sulfonyl or acetyl), or a weakly coordination ligand;

wherein M is manganese each of $R_1$-$RI_2$ is independently, halogen, heteroatom, alkyl, substituted alkyl, aryl, substituted aryl, heteroaryl, or a substituted heteroaryl group.

3. The method of claim 2, wherein the catalyst is linked to an inert solid support.

4. The method of claim 3, wherein the alkene has one of the following structures:

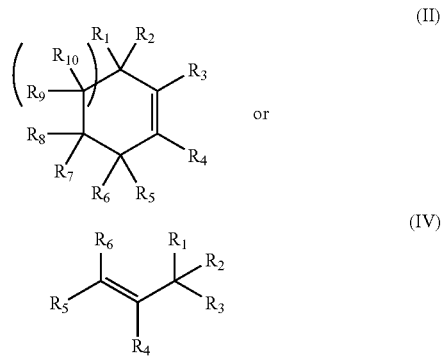

wherein $R_1$ is halogen, heteroatom, hydroxyl, alkoxy, substituted hydroxy, carboxyl, carbonyl, cyano, silyl, boro, phosphorus containing, sulfur containing, amino, substituted amino, nitro, alkyl, substituted alkyl, aryl, substituted aryl, heteroaryl, a substituted heteroaryl or phosphorous; wherein each of $R_2$-$R_{10}$ is individually hydrogen, halogen, heteroatom, hydroxy, alkoxy, substituted hydroxy, carboxyl, carbonyl, cyano, silyl, boro, phosphorus containing, sulfur containing, amino, carboxyl, carbonyl, cyano, amino, substituted amino, nitro, alkyl, substituted alkyl, aryl, substituted aryl, heteroaryl, or substituted heteroaryl groups; wherein $R_5$ and $R_6$ in formula II can also be an oxo group.

5. The method of claim 4, wherein the reaction is the presence of acetonitrile, water, dichloromethane, chloroform, methanol, t-butanol, benzene, toluene, xylene, chlorobenzene or mixtures thereof as solvent for the reaction.

6. The method of claim 5, wherein the reaction is conducted at a temperature ranging from about 0° C. to 60° C.

7. The method of claim 6, wherein the oxidant is hydrogen peroxide and the reaction is buffered by ammonium bicarbonate or sodium bicarbonate.

8. The method of claim 1, wherein the catalyst is linked to an inert solid support.

9. The method of claim 1, wherein the catalyst exhibits a product turnover number ranging from 50 to 3,000.

* * * * *